United States Patent
Band et al.

(10) Patent No.: US 7,326,814 B2
(45) Date of Patent: Feb. 5, 2008

(54) MINIMIZATION OF VOLATILE ORGANIC SULPHUR BYPRODUCTS IN DIMETHYL SULFATE QUATERNIZATION OF AMINES MADE WITH HYPOPHOROUS ACID

(75) Inventors: Elliot Band, Pleasantville, NY (US); Maurice Dery, Putnam Valley, NY (US); William Joyce, Hopewell Junction, NY (US); Jeffrey Earl Telschow, Croton-on-Hudson, NY (US); Biing Ming Su, Croton-on-Hudson, NY (US); Michael Engel, Mt. Kisco, NY (US); John Nowak, Yonkers, NY (US); Claude Peterson, Swan Lake, NY (US); Harold Providence, Brooklyn, NY (US); Phuong-Nga Trinh, Newtonville, MA (US); Sandra Urquhart, Paterson, NJ (US)

(73) Assignee: Akzo Nobel N.V., Arnhem (NL)

( * ) Notice: Subject to any disclaimer, the term of this patent is extended or adjusted under 35 U.S.C. 154(b) by 85 days.

(21) Appl. No.: 10/541,291

(22) PCT Filed: Dec. 23, 2003

(86) PCT No.: PCT/EP03/14890

§ 371 (c)(1),
(2), (4) Date: Dec. 6, 2005

(87) PCT Pub. No.: WO2004/060854

PCT Pub. Date: Jul. 22, 2004

(65) Prior Publication Data

US 2006/0189826 A1    Aug. 24, 2006

Related U.S. Application Data

(60) Provisional application No. 60/437,474, filed on Jan. 2, 2003.

(51) Int. Cl.
C07C 211/62 (2006.01)
C07C 211/63 (2006.01)
C07C 211/64 (2006.01)

(52) U.S. Cl. ...................................... 564/296
(58) Field of Classification Search .................... None
See application file for complete search history.

(56) References Cited

U.S. PATENT DOCUMENTS 3,146,267 A * 8/1964 Weinstein et al. .......... 564/282
5,670,677 A   9/1997 Ponsati Obiols et al. ... 554/114

FOREIGN PATENT DOCUMENTS

WO    WO 94/21596    9/1994

OTHER PUBLICATIONS

Database CAPLUS on STN, Acc. No. 1997:286285, Ogura et al., JP 09067320 (Mar. 11, 1997) (abstract).*
International Search Report, No. PCT/EP2003/014890, Apr. 26, 2004.

* cited by examiner

*Primary Examiner*—Brain Davis
(74) *Attorney, Agent, or Firm*—Ralph J. Mancini

(57) ABSTRACT

The present invention relates to a process for the minimization of volatile organic sulphur byproducts in dimethyl sulfate quaternization of amines made with hypophosphorous acid, which leads to the formation of an odor stable product.

12 Claims, No Drawings

MINIMIZATION OF VOLATILE ORGANIC SULPHUR BYPRODUCTS IN DIMETHYL SULFATE QUATERNIZATION OF AMINES MADE WITH HYPOPHOROUS ACID

The present case is based on International Application No. PCT/EP2003/014890 filed on Dec. 23, 2003, which claims priority of U.S. Provisional application No. 60/437,474 filed on Jan. 2, 2003.

FIELD OF THE INVENTION

The present invention relates to a process for the minimization of volatile organic sulphur byproducts in dimethyl sulfate quaternization of amines made with hypophorous acid, which leads to the formation of an odor stable product.

BACKGROUND OF THE INVENTION

Quaternized fatty acid triethanolamine ester salts are cationic surfactants which are excellent fabric-softeners that have high ecotoxicological compatibility. Ester quats are typically produced in a two-stage process in which triethanolamine is first partly esterified with fatty acids and the reaction product is subsequently alkylated or quaternized with an alkylating agent. Hypophosphorous acid and sodium hypophosphite are preferred catalysts for the esterification step. However, during working up, particularly at relatively high temperatures, certain by-products are formed, resulting in an adverse effect on the odor of the quaternized product. The present invention provides a process for the production of quaternized fatty acid triethanolamine ester salts having minimal odor problems. More specifically, the invention provides a process for the minimization of volatile organic sulphur byproducts in dimethyl sulfate quaternization of amines made with hypophorous acid, which leads to the formation of an odor stable product.

DETAILED DESCRIPTION OF THE INVENTION

The present invention relates to a process for the minimization of volatile organic sulphur byproducts in dimethyl sulfate quaternization of amines made with hypophorous acid, which leads to the formation of an odor stable product. The process of the invention is especially useful in the production of color- and odor-stable quaternized fatty acid triethanolamine ester salts.

Dimethyl Sulfate quaternaries are typically made in two steps. The first step is to esterfy the starting ethanolamine, for example triethanolamine, with fatty acid in the presence of an esterification catalyst/reductive bleaching agent, i.e., for example, hypophosphorous acid. The second step is to quaternize the esteramine with dimethylsulfate in order to form the ester quaternary ammonium compound. The synthesis of ester quaternaries can, however, result in a product that exhibits a foul objectionable odor. The present inventors have determined that the cause of this objectionable odor is a small amount of sulfur dioxide impurity in the dimethyl sulfate alkylating agent. More particularly, the sulfur dioxide impurity in the dimethyl sulfate is, under quaternization conditions, partially converted to hydrogen sulfide, methyl mercaptan, dimethyl sulfide and dimethyl disulfide, and other odor causing by-products in trace form. These undesirable by-products are the source of objectionable odors in the final product. Accordingly, the present invention is based on the discovery that sulfur dioxide is the source of odor by-products in the production of dimethyl sulfate quaternaries. By extension, if the sulfur dioxide is removed or minimized in the dimethyl sulfate, then the sulfur by-product concentrations will be minimized and improve the odor profile of the final product.

The present inventors have discovered a process for the production of odor stable products prepared from the dimethyl sulfate quaternization of amines made with hypophosphorous acid. Such products are odor stable because the volatile organic sulphur by-products which lead to the formation of objectionable odors are minimized. In this regard the invention comprises quaternizing said amines with a dimethyl sulfate quaternization agent wherein said dimethyl sulfate has a sulfur dioxide content of less than 10 parts per million (ppm), preferably less than 8 ppm, and still more preferably less than 5 ppm. Minimizing the sulfur dioxide content in the dimethyl sulfate quaternization agent reduces or eliminates the formation of undesirable odor causing by-products such as hydrogen sulfide, methyl mercaptan, dimethyl sulfide and dimethyl disulfide, resulting in a greatly improved odor profile of the final product. The present invention is not limited to processes for the preparation of ester quats but rather, is applicable to any dimethyl sulfate quaternization process of amines made with esterification catalyst/reductive bleaching agents.

The esterification catalyst/reductive bleaching agents employed in the context of the present invention are characterized in that they typically have a standard reduction potential of at least 0.5 volts. Nonlimiting examples of such esterification catalyst/reductive bleaching agents are hypophosphorous acid, sodium hypophosphite and mixtures thereof.

In another embodiment, the present invention relates to quaternary ammonium compounds having particularly good performance and stability profiles obtained by reaction of $C_{12}$-$C_{22}$ fatty acids or the hydrogenation products thereof, or a mixture of such acids, with an alkanolamine in the presence of an acid catalyst, wherein the ratio of fatty acid to alkanolamine is from about 1.40-2.0. The resultant esteramine reaction products are subsequently quaternized to obtain the quaternary ammonium salts of the present invention.

The fatty acid is preferably a $C_{16}$-$C_{22}$ acid containing a degree of unsaturation such that the iodine value ("IV") is in the range of from about 0-140, preferably, from about 3-90, more preferably in the range of 40-60 and still more preferably, in a range of from about 45-55. Preferably, the fatty acid source is selected from $C_{12}$-$C_{22}$ fatty acids represented by the formula:

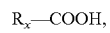

wherein, $R_x$ is a $C_{11}$-$C_{21}$ alkyl group.

Preferred sources of $C_{12}$-$C_{22}$ fatty acids are selected from the group consisting of: lauric acid, tridecylic acid, myristic acid, pentadecylic acid, palmitic acid, margaric acid, stearic acid, arachidic acid, phytanic acid, behenic acid, anionic derivatives thereof, salts thereof, and combinations thereof.

Preferred sources of acid are $C_{12}$-$C_{22}$ fatty acids comprising a saturated alkyl group. Other preferred sources of acids are $C_{12}$-$C_{22}$ fatty acids comprising an unsaturated group, typically having an iodine value of from 15 to 25, preferably from 18 to 22.

The source of acid may be selected from the group consisting of palmitoleic acid, oleic acid, elaidic acid, vaccenic acid, linoleic acid, cis-eleostearic acid, trans-eleostearic acid, linolenic acid, arachidonic acid, anionic derivatives thereof, salts thereof, and combinations thereof.

Preferred sources of fatty acids are selected from the group consisting of coconut, soybean, tallow, palm, palm kernel, rapeseed, lard, sunflower, corn, safflower, canola, olive, peanut, and combinations thereof. A preferred source of acid is hard tallow fatty acid and/or partially hydrogenated tallow fatty acid.

Preferred fatty acids include but are not limited to oleic, palmitic, erucic, eicosanic and mixtures thereof. Soy, tallow, palm, palm kernel, rape seed, lard, mixtures thereof and the like are typical sources for fatty acid which can be employed in the present invention. The fatty acid(s) employed in the present process optionally have a cis to trans isomer ratio of from about 80:20 to about 95:5. In another embodiment, the trans isomer content of said fatty acid(s) is less than about 10%. An typical trans-isomer content is between about 0.5-9.9%. A preferred fatty acid is a mixture of tallow/distilled tallow having a cis:trans isomer ratio of greater than 9:1. Partial or fully hydrogenated fatty acids can be employed in the process of the present invention.

The alkanolamines employable in the present invention generally correspond to the formula:

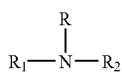

herein R, $R_1$ and $R_2$ are independently selected from $C_2$-$C_6$ hydroxyalkyl groups or a group of the formula

where $R_3$ is independently H or a $C_1$ to $C_4$ alkyl and z is 1 to 10.

Alternatively, the alkanolamines can be of the formula:

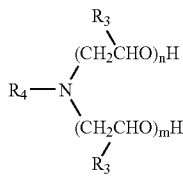

Where $R_4$ is a linear or branched, substituted or unsubstituted alkyl group, amidoalkyl group, etheralkyl group, or polyoxyalkylene group, n and m=1-10, and $R_3$ has the meanings defined above.

Examples of alkanolamines useful in the context of the present invention include, but are not limited to, triethanolamine, propanol diethanolamine, ethanol diisopropanolamine, triisopropanol amine, diethanolisopropanol amine, diethanolisobutanolamine, methyl diethanolamine and mixtures thereof.

The molar ratio of fatty acid to alkanol amine is generally in the range of from about 1.4 to 2.0, preferably from about 1.55-1.90, and more preferably, in the range of from about 1.65-1.75. Best results are usually obtained when the molar ratio is between about 1.68-1.72. The acid catalyst employable in the present process includes, but is not limited to, acid catalysts such as sulfuric acid, phosphorous acid, p-toluene sulphonic acid, methane sulphonic acid, oxalic acid, hypophosphorous acid or an acceptable Lewis acid in an amount of 500-3000 ppm based on the amount of fatty acid charge. A preferred acid catalyst is hypophosphorous acid. Typically, 0.02-0.2% by weight, and more preferably 0.1 to 0.15% by weight of acid catalyst, based on the weight of fatty acid, in employed in the present process.

The esterification of fatty acids with alkanolamines is carried out at a temperature of from about 150°-250° C. until the reaction product has an acid value of below 5. After the esterification, the crude product is reacted with alkylating agents in order to obtain the quaternary ammonium product. The alkylating agent employed in the present invention is dimethyl sulfate having a sulfur dioxide content of less than about 20 ppm, in another embodiment less than 10 ppm, in another embodiment less than 8 ppm, and in yet another embodiment less than 5 ppm. Typically, 0.7 to 1.0, preferably 0.75 to 0.98 mol dimethyl sulfate per mole of esteramine is satisfactory in yielding the quaternized product.

The quaternization may be carried out in bulk or in solvent, at temperatures ranging from 60°-120° C. If a solvent is employed, then the starting materials and/or product must be soluble in the solvent to the extent necessary for the reaction. Solvents of this type are generally known in the art. Suitable examples include polar solvents such as, for example, lower alcohols, i.e., $C_1$-$C_6$ alcohols. Other solvents which can be employed include, but are not limited to mono-, di-, and tri-glycerides, fatty acids, glycols and mixtures thereof.

The products of the invention can beneficially be employed in textile softening and/or personal care compositions and in other applications typical for cationic surfactants.

The invention will now be illustrated by the following non-limiting examples.

EXAMPLE 1

Quaternization of TEEMA (Tallow Fatty Acid Esters of Triethanolamine)

In a 500 ml 3-necked flask we placed 250.3 g (0.386 mol) of HT (hardened tallow) TEEMA (Pilot Plant batch 2279) containing 320 ppm of residual hypophosphorous acid. We treated this at 75-90° with a total of 45.6 g (0.361 mol) of dimethyl sulfate containing 7 ppm of sulfur dioxide by GC analysis. After the addition, the reaction was held at 90° for 1 hr before 30 g of isopropyl alcohol was added to make the final TEQ (methyl quaternary ammonium salt of triethanolamine esters).

COMPARATIVE EXAMPLE 1

We used the same procedure and ingredients of Example 1 except that standard commercial dimethyl sulfate containing 984 ppm of sulfur dioxide was employed.

The TEQ from the above examples was formulated into fabric softener compositions whose odors were compared by a panel. In addition, both quat samples were analyzed for sulfur-containing species by GC. Results are summarized in the table below.

| TEQ Made from Low- and High-SO2 DMS | | |
|---|---|---|
| Analysis | Example 1 | Comp. Ex. 1 |
| SO2 in DMS | 7 ppm | 984 ppm |
| Malodor detected? | No | Yes |
| CH3SH by GC | Not detected (<2 ppb) | 6 ppb |

The invention claimed is:

1. A process for the minimization of odor in dimethyl sulfate quaternization of amines made with hypophorous acid which comprises conducting said quaternization in the presence of dimethyl sulfate, wherein said dimethyl sulfate contains less than 20 ppm sulfur dioxide.

2. The process of claim 1 wherein said odor is caused by volatile organic sulphur byproducts.

3. The process of claim 2 wherein said dimethyl sulfate contains less than 8 ppm sulfur dioxide.

4. The process of claim 3 wherein said dimethyl sulfate contains less than 5 ppm sulfur dioxide.

5. A process for preparing an ester quaternary having improved odor profile with comprises esterfying an alkanol amine with fatty acid in the presence of a esterification catalyst/reductive bleaching agent having a standard reduction potential of at least 0.5 volts in order to form an esteramine and thereafter quaternizing said esteramine with dimethylsulfate, wherein said dimethyl sulfate contains less than 20 ppm sulfur dioxide.

6. The process of claim 5 wherein said esterification catalyst/reductive bleaching agent is selected from the group consisting of hypophosphorous acid, sodium hypophosphite and mixtures thereof.

7. The process of claim 6 wherein said fatty acid is a $C_{16}$-$C_{22}$ acid containing a degree of unsaturation such that the iodine value ("IV") is in the range of from about 0-140.

8. The process of claim 7 wherein said fatty acid is selected from the group consisting of oleic, palmitic, erucic, eicosanic and mixtures thereof.

9. The process of claim 8 wherein said alkanol amine is of the formula:

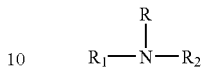

wherein R, $R_1$ and $R_2$ are independently selected from $C_2$-$C_6$ hydroxyalkyl groups.

10. The process of claim 9 wherein said alkanolamine is selected from the group consisting of triethanolamine, propanol diethanolamine, ethanol diisopropanolamine, triisopropanol amine, diethanolisopropanol amine, diethanolisobutanolamine, methyl diethanolamine and mixtures thereof.

11. The process of claim 5 wherein said dimethyl sulfate contains less than 8 ppm sulfur dioxide.

12. The process of claim 11 wherein said dimethyl sulfate contains less than 5 ppm sulfur dioxide.

* * * * *

UNITED STATES PATENT AND TRADEMARK OFFICE
CERTIFICATE OF CORRECTION

PATENT NO. : 7,326,814 B2
APPLICATION NO. : 10/541291
DATED : February 5, 2008
INVENTOR(S) : Elliot Band et al.

Page 1 of 1

It is certified that error appears in the above-identified patent and that said Letters Patent is hereby corrected as shown below:

Col. 5, line 14, change "with" to --which--.

Col. 5, line 15, change "a" to --an--.

Signed and Sealed this

First Day of September, 2009

David J. Kappos
*Director of the United States Patent and Trademark Office*